(12) United States Patent
East

(10) Patent No.: US 7,776,263 B2
(45) Date of Patent: Aug. 17, 2010

(54) APPARATUS FOR PROVIDING HOMOGENEOUS DISPERSIONS

(75) Inventor: Richard C. East, Dallas, TX (US)

(73) Assignee: Abbott Laboratories Inc., Abbot Park, IL (US)

( * ) Notice: Subject to any disclaimer, the term of this patent is extended or adjusted under 35 U.S.C. 154(b) by 897 days.

(21) Appl. No.: 11/258,986

(22) Filed: Oct. 26, 2005

(65) Prior Publication Data

US 2006/0093519 A1    May 4, 2006

Related U.S. Application Data

(60) Provisional application No. 60/623,273, filed on Oct. 29, 2004.

(51) Int. Cl.
*G01N 21/00* (2006.01)
(52) U.S. Cl. .............................. 422/64; 422/50; 422/58; 422/62; 422/63; 422/65
(58) Field of Classification Search ................... 422/63, 422/64, 65, 102, 103
See application file for complete search history.

(56) References Cited

U.S. PATENT DOCUMENTS

| | | | |
|---|---|---|---|
| 2,510,858 A * | 6/1950 | Black | .......................... 366/208 |
| 2,573,339 A | 10/1951 | Kantor | |
| 3,537,794 A | 11/1970 | Louder | |
| 3,754,737 A | 8/1973 | O'Dea | |
| 3,755,931 A | 9/1973 | Gisler | |
| 3,768,727 A | 10/1973 | Proni | |
| 3,848,796 A | 11/1974 | Bull | |
| 3,882,716 A | 5/1975 | Beiman | |
| 3,977,272 A | 8/1976 | Neumann | |
| 4,061,019 A | 12/1977 | Blasetti | |
| 4,156,383 A | 5/1979 | Maddox | |
| 4,373,029 A | 2/1983 | Nees | |
| 4,699,766 A | 10/1987 | Yamashita | |
| 4,715,246 A | 12/1987 | Hartmann | |
| 4,731,225 A | 3/1988 | Wakatake | |
| 4,740,001 A | 4/1988 | Torleumke | |
| 4,806,197 A | 2/1989 | Harvey | |
| 4,849,176 A | 7/1989 | Sakagami | |
| 4,852,415 A | 8/1989 | Bogatzki et al. | |
| 4,906,433 A | 3/1990 | Minekane | |
| 5,104,807 A | 4/1992 | Mitsumaki et al. | |
| 5,104,808 A | 4/1992 | Laska et al. | |

(Continued)

FOREIGN PATENT DOCUMENTS

EP    0 067 943 B1    12/1982

(Continued)

OTHER PUBLICATIONS

Mobley "Gears and Gear Drives". Plant Engineer's Handbook. 2001. pp. 57/1029-57/1042.*

*Primary Examiner*—Yelena G Gakh
*Assistant Examiner*—David Weisz
(74) *Attorney, Agent, or Firm*—David L. Weinstein

(57) ABSTRACT

An apparatus for mixing a liquid in a container in order to provide a homogeneous solution or suspension of the liquid in the container. In particular, the apparatus of this invention can be used to provide a homogenous dispersion of particulate material in a liquid medium.

6 Claims, 13 Drawing Sheets

U.S. PATENT DOCUMENTS

| | | | |
|---|---|---|---|
| 5,178,834 A | | 1/1993 | Kagayama et al. |
| 5,314,125 A | * | 5/1994 | Ohno .......................... 241/175 |
| 5,316,745 A | * | 5/1994 | Ting et al. ................... 422/295 |
| 5,580,524 A | | 12/1996 | Forrest et al. |
| 5,985,672 A | * | 11/1999 | Kegelman et al. ............. 436/50 |
| 6,299,567 B1 | | 10/2001 | Forrest et al. |
| 6,436,349 B1 | | 8/2002 | Carey et al. |
| 6,562,298 B1 | | 5/2003 | Arnquist et al. |

FOREIGN PATENT DOCUMENTS

| | | |
|---|---|---|
| GB | 2 081 118 A | 2/1982 |

* cited by examiner

APPARATUS FOR PROVIDING HOMOGENEOUS DISPERSIONS

This application claims priority to U.S. Provisional Application No. 60/623,273, filed on Oct. 29, 2004.

BACKGROUND OF THE INVENTION

1. Field of the Invention

This invention relates to the field of mixing liquids to form a homogenous suspension or solution. More particularly, this invention further relates to the field of mixing liquids containing particulate material in order to obtain a homogeneous suspension of particulate material in the liquid.

2. Discussion of the Art

Automated instrumentation has been developed for performing assays in clinical laboratories. Automated instrumentation has been used in the area of immunoassays. In the area of immunoassays, certain reagents known as solid-phase reagents are used in heterogeneous immunoassays. In heterogeneous immunoassays, the solid-phase reagent can include paramagnetic particles, while another reagent, the labeled reagent, can include a chemiluminescent label. In order to obtain accurate and precise assays results, the solid-phase reagent must exist as a uniform, homogeneous dispersion as particles in a dispersing medium. One problem encountered when using solid-phase reagents is that over a period of time, the particulate material in the reagent tends to settle out of the dispersion. Therefore, there is a need to re-disperse the particulate material of the solid-phase reagent in the dispersing medium. In an automated system, the solid-phase reagent must be re-dispersed by the apparatus, without manual shaking by an operator. Many references in the prior art indicate apparatus and methods for maintaining solid particulate material in a uniform, homogeneous dispersion.

U.S. Pat. No. 5,104,807 describes an apparatus in which a train of containers is provided on a movable holder. The train is conveyed such that it passes through a container rotating area and a container non-rotating area. The motion of the movable holder driven by a driving source is transmitted to the containers located in the container rotating area as a rotational force of the containers on their own axes. In the container non-rotating area, a light beam of a photometer is formed so that light measurement can be performed to measure the test solutions in the containers which arrived at the non-rotating area.

U.S. Pat. No. 3,848,796 discloses a sedimentation rate centrifuge comprising a centrifuge head, a driven shaft mounting the head for rotation therewith and a drive motor coupled to the driven shaft for imparting rotative motion thereto about the axis of the each in intermittent periods of predetermined duration to generate centrifugal force applicable in a direction generally normal to its axis of rotation. The centrifuge head comprises a body, a sample tube holder carried by the body near the periphery thereof, the sample tube holder constructed and arranged to receive elongate sample tubes each containing a thin column of blood and each vertically arranged and oriented substantially parallel to the axis or rotation of the body so that the centrifugal force is applied laterally to the long axis of the sample tubes, means for causing periodic rotation of the sample tube holder and the associated sample tube about its own long axis between each application of centrifugal force and when the body is substantially at rest.

UK Patent Application GB 2 081 118 describes the simultaneous mixing of the contents in each of a plurality of containers each including a liquid. The mixing is effected by simultaneously causing the containers each to be rotated about its own axis first in one direction and then in another. In one embodiment the test tubes are mounted in a turntable with a disc-shaped drive member frictionally engaging each tube and rotatable (independently of turntable) to cause each tube to be rotated about its own axis to mix the contents therein. The turntable assembly is particularly suitable for use with automated analysis machines.

U.S. Pat. No. 6,436,349 describes a reagent transport apparatus for use on a clinical analyzer. The reagent transport apparatus comprises a base, a reagent tray mounted on the base for rotation about a primary vertical axis of rotation; a drive motor for rotating the reagent ray about the primary vertical axis of rotation; a control unit in the form of a computer circuit for operating the drive motor to selectively position a selected one of the reagent containers at the reagent aspiration point; a plurality of mounting assemblies disposed in a first circle on the reagent ray, concentric with the primary vertical axis of rotation; a plurality of agitating assemblies disposed in a second circle on the reagent ray, concentric with the primary vertical axis of rotation, each of the agitating assemblies having a respective secondary vertical axis of rotation; and agitating motor for rotating each of the plurality of agitating assemblies about the respective secondary vertical axis of rotation, each agitating assembly comprising a first reagent container holder mounted on the reagent tray for rotation about the respective secondary vertical axis of rotation, the reagent transport assembly further comprising a ring gear, concentric with the primary vertical axis of rotation and coupled to the agitating motor, in driving engagement with each of the satellite gears wherein rotation of the ring gear by the agitating motor about the primary vertical axis causes each of the satellite gears to rotate about the respective secondary vertical axis.

SUMMARY OF THE INVENTION

This invention provides an apparatus for mixing a liquid in a container in order to provide a homogeneous solution or suspension of the liquid in the container. In particular, the apparatus of this invention can be used to provide a homogenous dispersion of particulate material in a liquid medium.

In one aspect, the apparatus comprises a plurality of rotatable seats, each seat capable of supporting a container that contains a liquid. Each rotatable seat comprises a platform for supporting the container. The platform has a top major surface and a bottom major surface. The platform of each rotatable seat is preferably cylindrical in shape, wherein the top major surface and the bottom major surface preferably have circular geometry. A shaft projects from the bottom major surface of the platform of each rotatable seat, and, attached to the shaft are at least one sprocket wheel and at least one bearing. A chain, which chain is driven by a different sprocket wheel, i.e., the drive sprocket wheel, causes the sprocket wheel attached to the shaft shaft projecting from the bottom major surface of the platform of the rotatable seat to rotate. The shaft of the rotatable seat rotates in the bearing(s), whereby the platform of the rotatable support rotates. A container seated upon the top major surface of the platform of the rotatable seat is thus enabled to rotate, whereby the contents of the container can be agitated.

In one embodiment, the plurality of rotatable seats can be arranged in a circle on a carousel, and the chain can engage the sprockets of the sprocket wheels attached to the shafts associated with the rotatable seats. By this arrangement, the rotatable seats can be rotated when the chain is driven by the drive sprocket wheel.

The use of a chain and a drive sprocket wheel for rotating rotatable seats for supporting reagent containers exhibits numerous benefits. One benefit involves reduction of the weight of the carousel, thereby decreasing the rate of wear of the components that support the carousel. Another benefit involves reduction of acoustic noise relative to that produced by a gear-driven agitating system. A third benefit involves reduction of cost relative to that of a gear-driven agitating system. A fourth benefit involves reduction of the inertial load on the agitating motor relative to that of a gear-driven agitating system. A fifth benefit involve the elimination of the need for a lubricant, as is required in a gear-driven agitating system.

DETAILED DESCRIPTION

As used herein, the term "carousel" means a tray capable of holding a plurality of containers. The expression "reagent container" generally means a container that contains a solid-phase reagent or a labeled reagent, also known as a tracer reagent. However, the expression "reagent container" can also include containers for diluents and for reagents other than the types mentioned previously. The expression "sprocket wheel" means a wheel rimmed with sprockets, used to engage the links of a chain in a pulley or drive system. The expression "drive sprocket wheel" means a sprocket wheel that causes the chain in a pulley or drive system to move. The term "sprocket" means any of various toothlike projections arranged on the rim of a wheel to engage the links of a chain. The expression "diametric pitch" means pitch diameter divided by the number of sprockets.

Figure 1A:
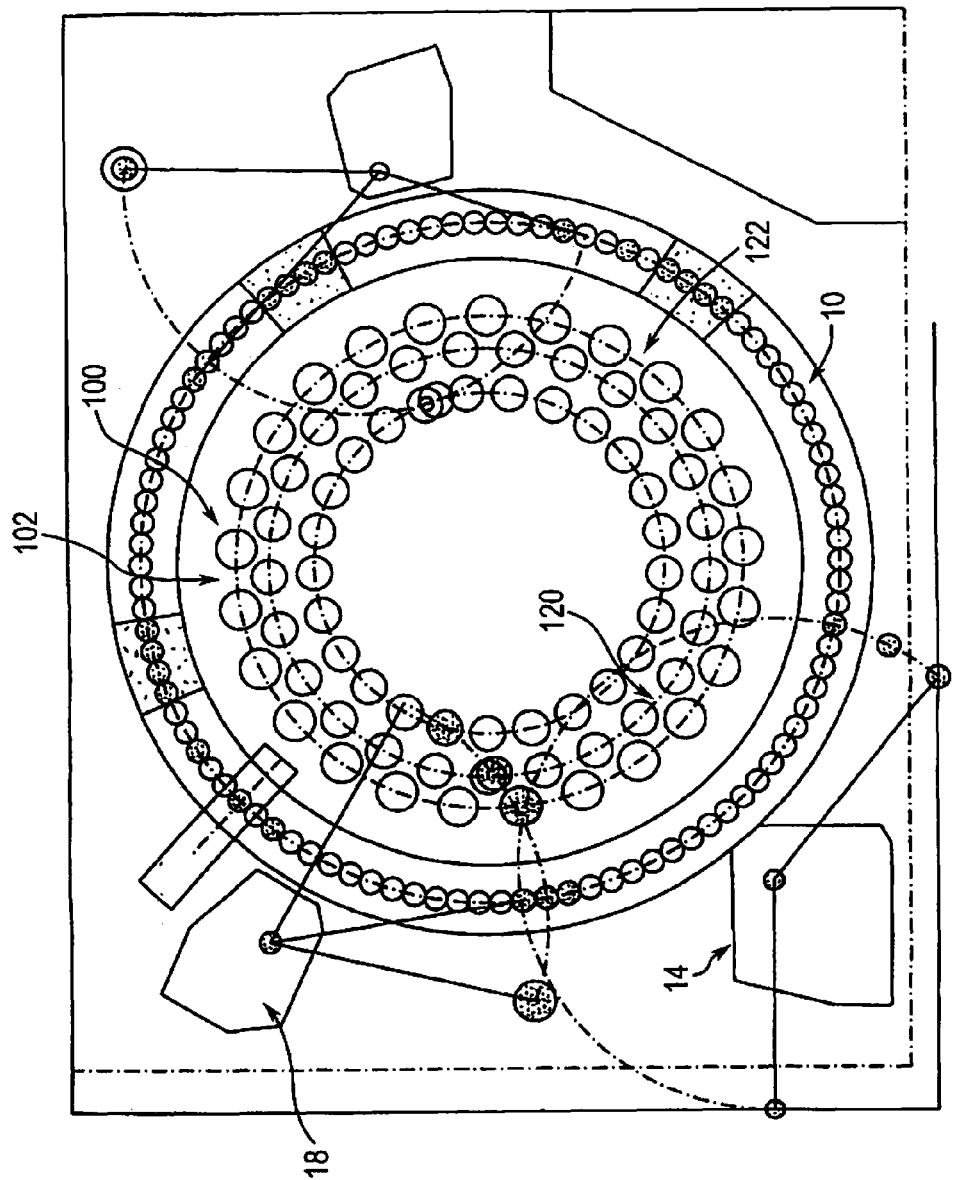
FIG. 1A is a schematic view of an immunoassay apparatus of the prior art that can employ the reagent transport apparatus of this invention. The schematic view is a top plan view.

An immunoassay can be used to determine the presence or concentration of an item of interest in a sample. In the article described in U.S. Pat. No. 6,562,298, incorporated herein by reference, to perform an immunoassay (as shown in FIG. 1A herein), a reaction container (not shown) is moved into a process lane 10 at a first position. At the first position, a known quantity of sample, e.g., 50 µL of blood, is deposited in the reaction container by a filling system 14. The filling system comprises a pipette (not shown), which may be mounted on an arm for vertical movement and angular movement. After the reaction container is indexed to arrive at a second position, a known quantity of a first reagent is deposited into the reaction container by a second filling system 18. The first reagent can contain magnetically responsive microparticles coated with antibodies or other binding substances that specifically bind to the item of interest in the sample. The first reagent may be added with an assay specific diluent. In some cases, the first reagent and a conjugate can be added at the second position.

At a third position, a mechanical device (not shown) is provided to mechanically move the reaction container and cause mixing of the contents in the container. Further treatment of the reaction mixture and performance of the immunoassay are described in U.S. Pat. No. 6,562,298, previously incorporated herein by reference. U.S. Pat. No. 6,562,298 also shows a reaction container suitable for use with this invention, a process lane suitable for use with this invention, and a mechanical device for moving the reaction container that is suitable for use with this invention.

Referring now to FIGS. 1A, 1B, 2, 3, 4, 5, and 6, a reagent transport apparatus 100 provides a carousel 102 for a plurality of reagent containers. Reagent containers that are suitable for this invention are described in U.S. Pat. No. 6,562,298, previously incorporated herein by reference. In particular, see column 13, line 35 through column 14, line 37 and FIGS. 22, 23A, 23B, 23C, 24A, 24B, and 25 of U.S. Pat. No. 6,562,298. At least some of the reagent containers contain solid-phase reagents. These containers are periodically agitated to maintain homogeneous dispersions of the solid-phase reagents. The reagent containers have at least one agitator fin, and preferably a plurality of agitator fins, molded into their inner walls. The reagent containers can also have machine-readable labels, e.g., bar code labels, attached thereto. A bar code reader can be used to record such data as the loaded position of each particular reagent in a reagent container, the identity of each particular reagent in a reagent container, the lot number of each particular reagent in a reagent container. Containers for tracer or labeled reagent can be used with the carousel 102 described herein, with carousels adjacent to and concentric with the carousel 102 described herein, or with some other type of reagent transport component. These containers can be loaded onto designated positions on the carousel 102 described herein, onto carousels adjacent to and concentric with the carousel 102 described herein, or onto some other type of reagent transport component. Reagent containers can be loaded directly from a storage area.

A bar code reader, e.g., a laser bar code reader, records various data relating to the reagent containers, such as, for example, the loaded position of each particular reagent in a reagent container, the identity of each particular reagent in a reagent container, the lot number of each particular reagent in a reagent container. Such recordation of data enables random loading of the reagent containers.

Probes for aspirating reagents from reagent containers and dispensing reagents into reaction containers are described in U.S. Pat. No. 6,562,298, previously incorporated herein by reference. Volumes of reagent used depend upon the particular assay, and specific reagents can be added to the reaction container by an appropriate reagent probe. Probes for dispensing reagents are preferably thoroughly washed with deionized water between dispensings.

In addition to the carousel 102, the reagent transport apparatus comprises a base (not shown) and at least one motor 106, e.g., a stepper motor, fixed to the base by suitable fasteners for driving the carousel 102 about the central axis of the carousel 102.

The carousel 102 is supported by a plurality of v-wheels 108, typically three in number, secured by bolts, e.g., shoulder bolts, to the base of the reagent transport apparatus. In the embodiment described herein, two v-wheels are in fixed locations, while the position of a third v-wheel relative to the carousel 102 can be varied by a biasing element, e.g., a spring. When the carousel 102 is positioned for rotation about its central axis, all three v-wheels 108 engage a v-shaped projection located near the bottom of the inner wall 110 of the carousel 102.

Figure 2:
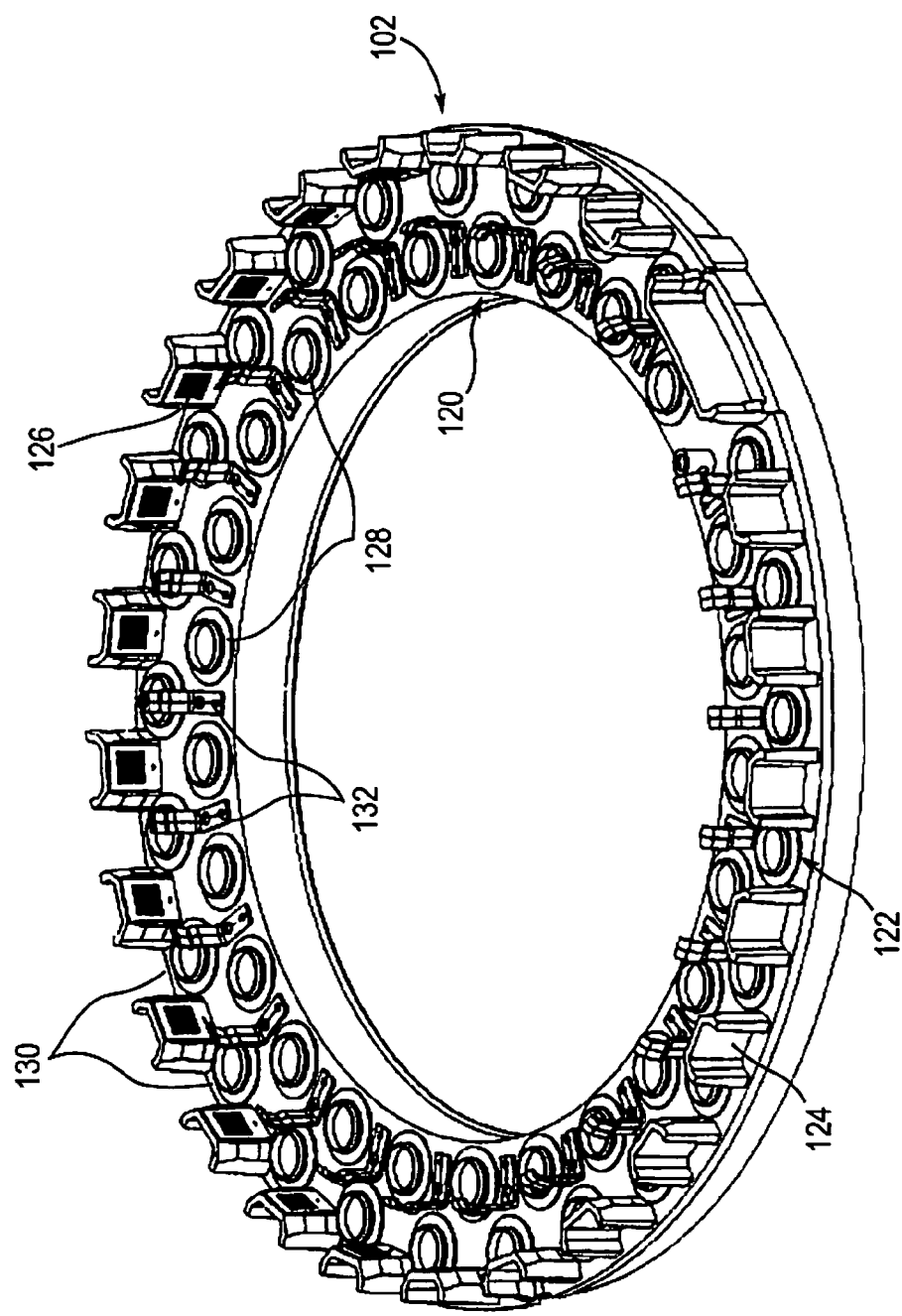
FIG. 2 is a perspective view of a carousel showing placement of seats for holding containers that are to be agitated and placement of seats for containers that need not be agitated.
Figure 3:
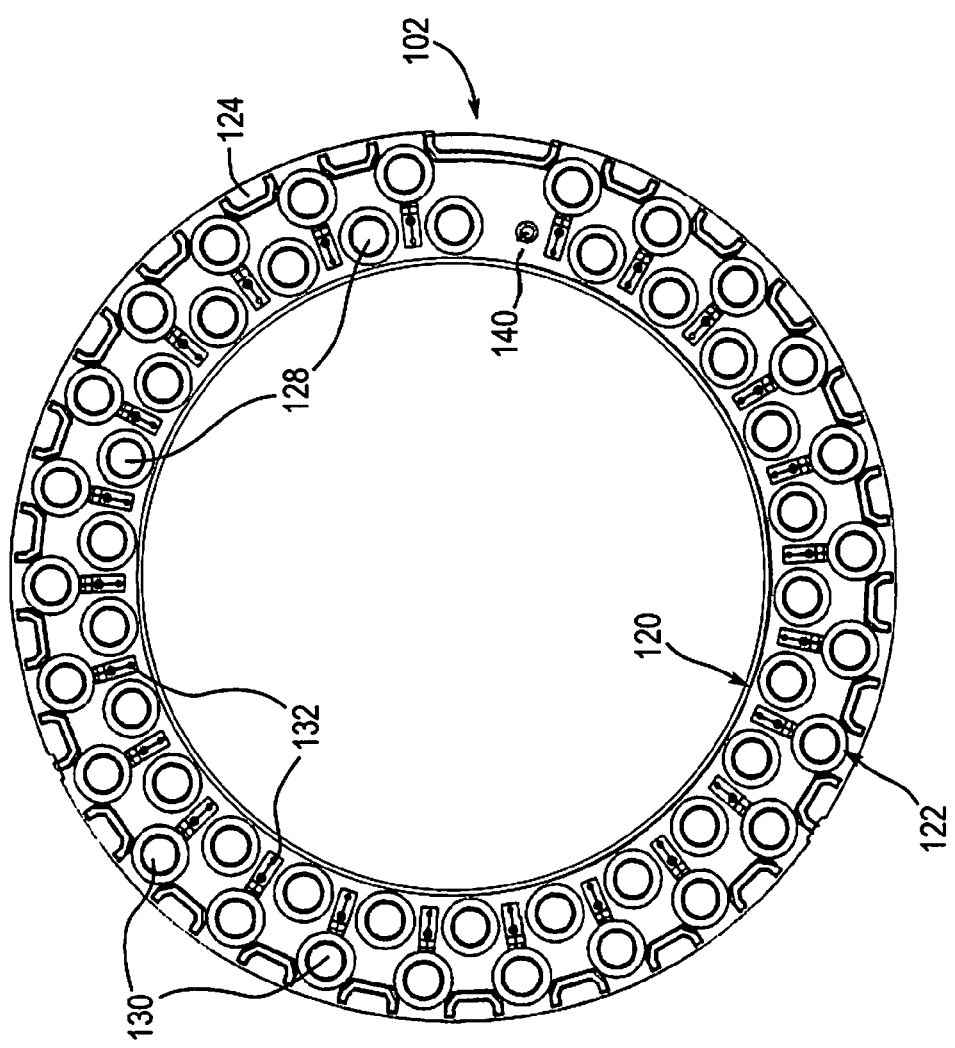
FIG. 3 is a top plan view of the carousel of FIG. 2.
Figure 4:
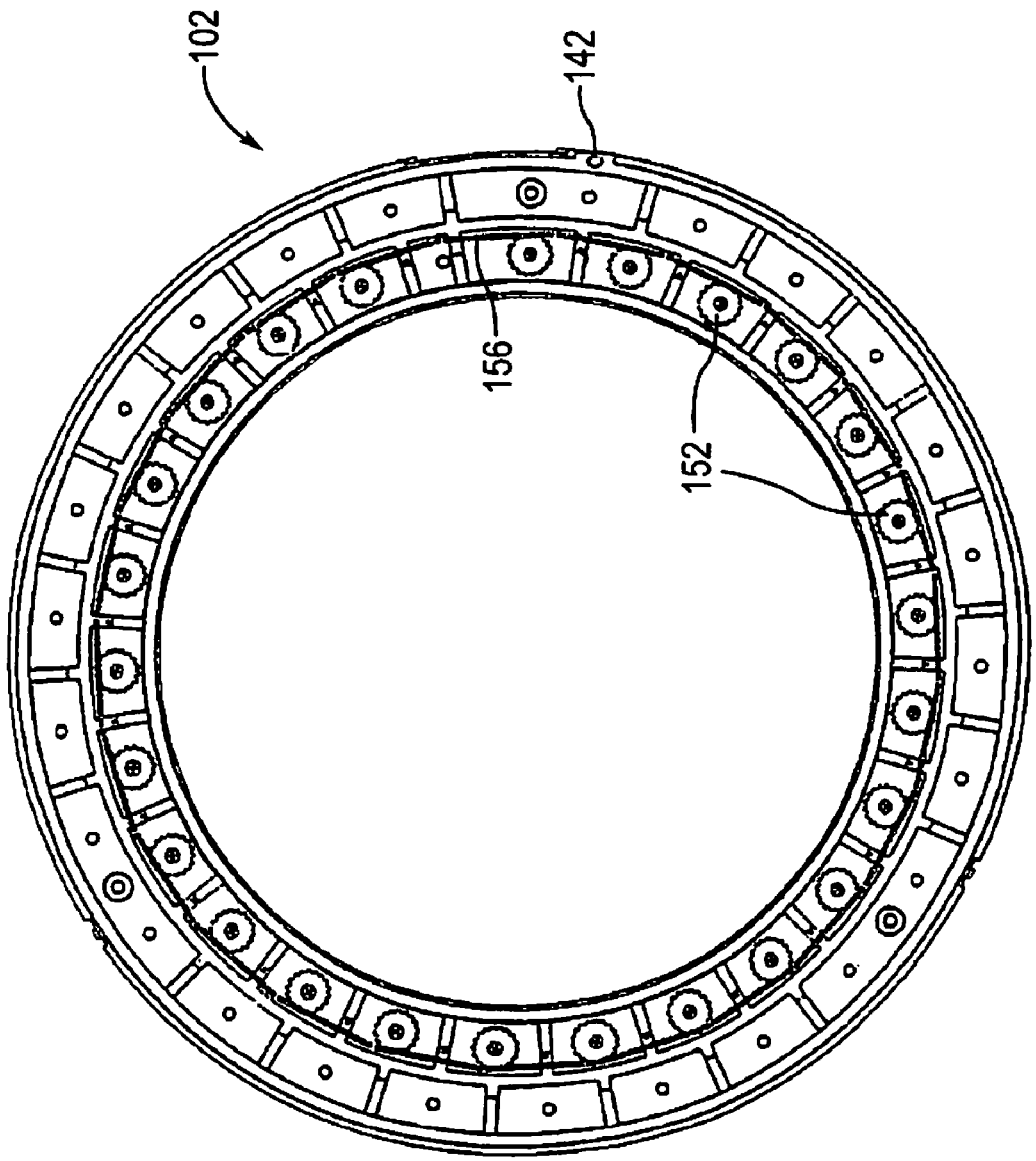
FIG. 4 is a bottom plan view of the carousel of FIG. 2.

In the embodiment shown in FIGS. 2 and 3, the carousel 102 has an inner ring 120 of seats and an outer ring 122 of seats. In addition, the carousel 102 has a plurality of projections 124 for displaying machine-readable labels 126, e.g., bar code labels. The machine-readable labels 126, when read by a reader, such as, for example, a bar code reader, notify the system as to the absence of a container in the inner ring 120. This notification accelerates initialization of the system.

The inner ring 120 of seats is concentric with the outer ring 122 of seats. Each seat 128 in the inner ring 120 can contain a reagent container. In this embodiment, these seats 128 are designed to be rotated in order to agitate the contents of a reagent container mounted thereon. Each seat 130 in the outer ring 122 can also contain a reagent container. However, these seats 130 are not designed to be rotated in such a manner as to agitate the contents of a container mounted thereon. The rotatable seats 128 on the inner ring 120 are supported by at least one bearing, which will be described later.

As shown in FIGS. 2 and 3, there are a total of 50 positions for containers on the carousel 102. Twenty-five of these positions are located on the inner concentric ring 120 and another twenty-five are located on the outer concentric ring 122.

Figure 1B:
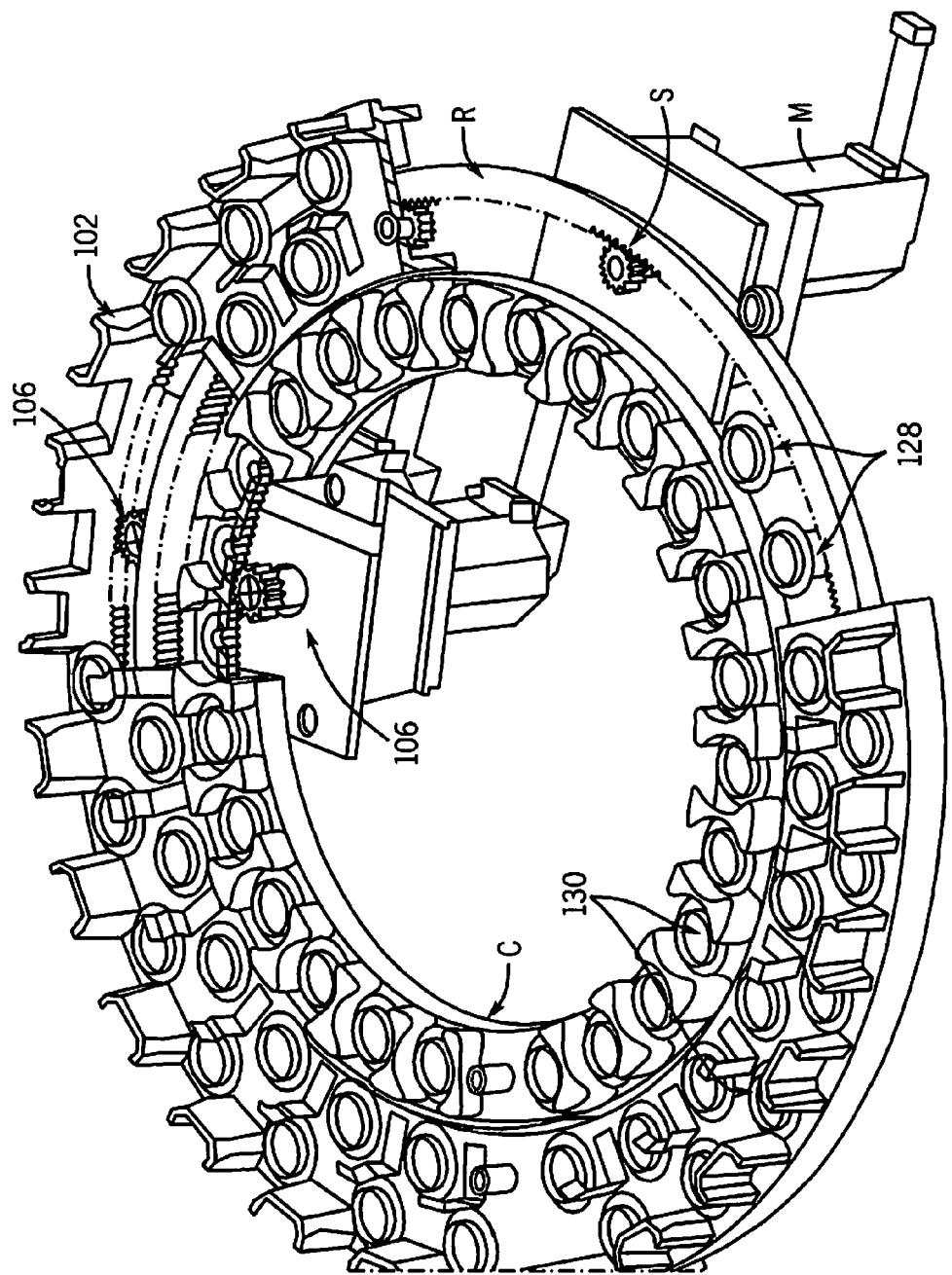
FIG. 1B is a perspective view of the carousels of the immunoassay apparatus of FIG. 1A. Also shown in FIG. 1B are motors that drive the carousels and the motor that drives the mechanisms that agitate the reagent containers.

Referring to FIG. 1B, which depicts a carousel system of the prior art, the carousel 102, which is also shown in FIG. 1A, is shown in the operating environment that is used in the ARCHITECT i2000/i2000SR apparatus, manufactured by Abbott Laboratories. FIG. 1B also shows rotatable seats 128 and fixed seats 130 of the type suitable for use in the present invention. In FIG. 1B, the containers seated on the rotatable seats 128 are agitated by means of movement of a ring gear "R", which is driven by a satellite gear "$S_0$", which is driven by a motor "M". The ring gear "R" causes the satellite gears "$S_1, S_2, \ldots, S_n$" to rotate about their own axes. Both the carousel 102 and a second carousel "C" are driven by the motor 106, which motor is of the type suitable for use in the present invention. The motors 106 and "M" are mounted on the base (not shown). The operating environment of the ARCHITECT i2000/i2000SR apparatus can be used in the present invention, without the ring gear "R", and without the satellite gears "$S_0$" and "$S_1, S_2, \ldots, S_n$".

Figure 10:
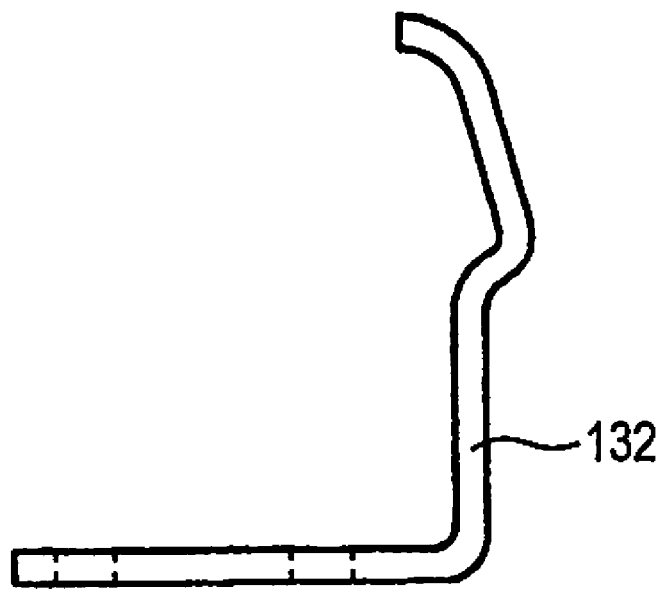
FIG. 10 is a side view in elevation of a retention element for securing oversized containers.
Figure 12:
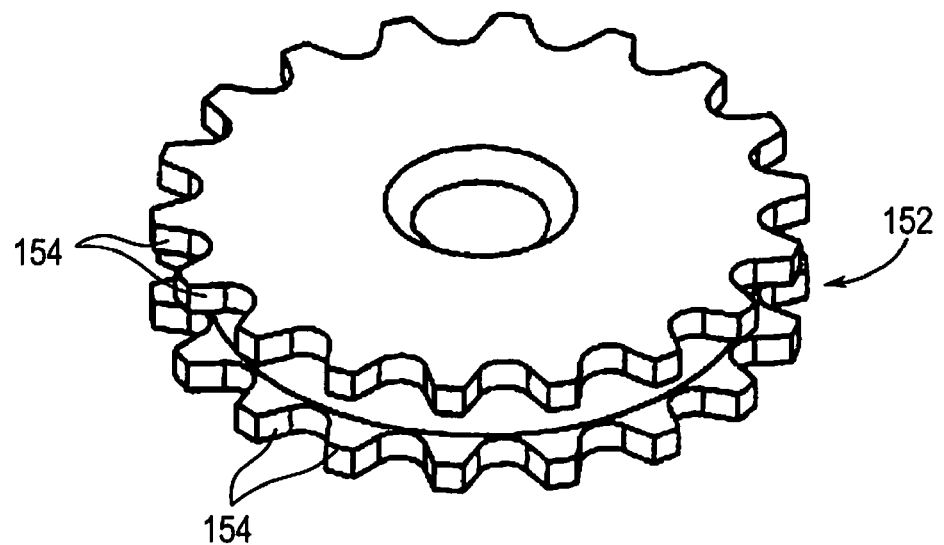
FIG. 12 is a perspective view of a sprocket wheel associated with a rotatable seat.
Figure 11:
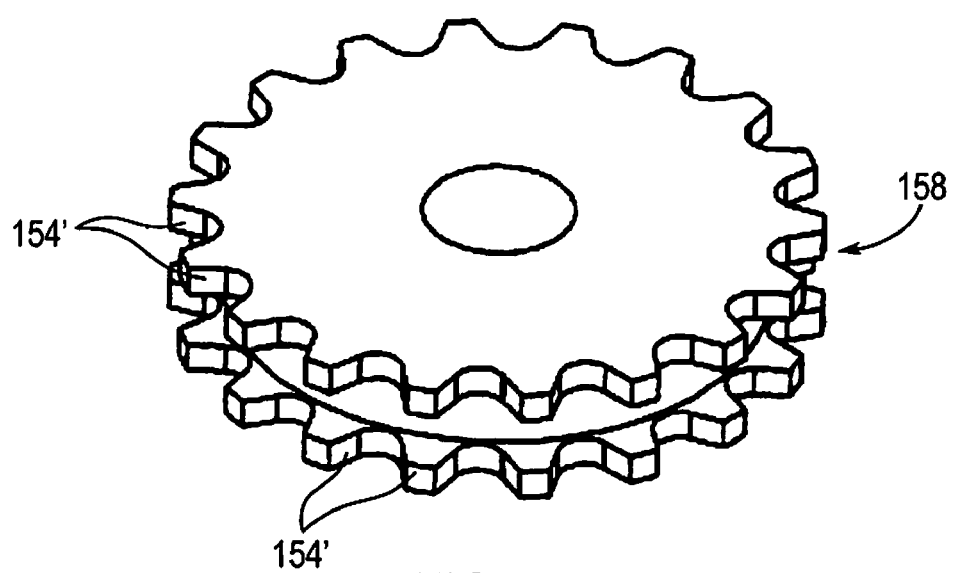
FIG. 11 is a perspective view of a drive sprocket wheel.
Figure 13:
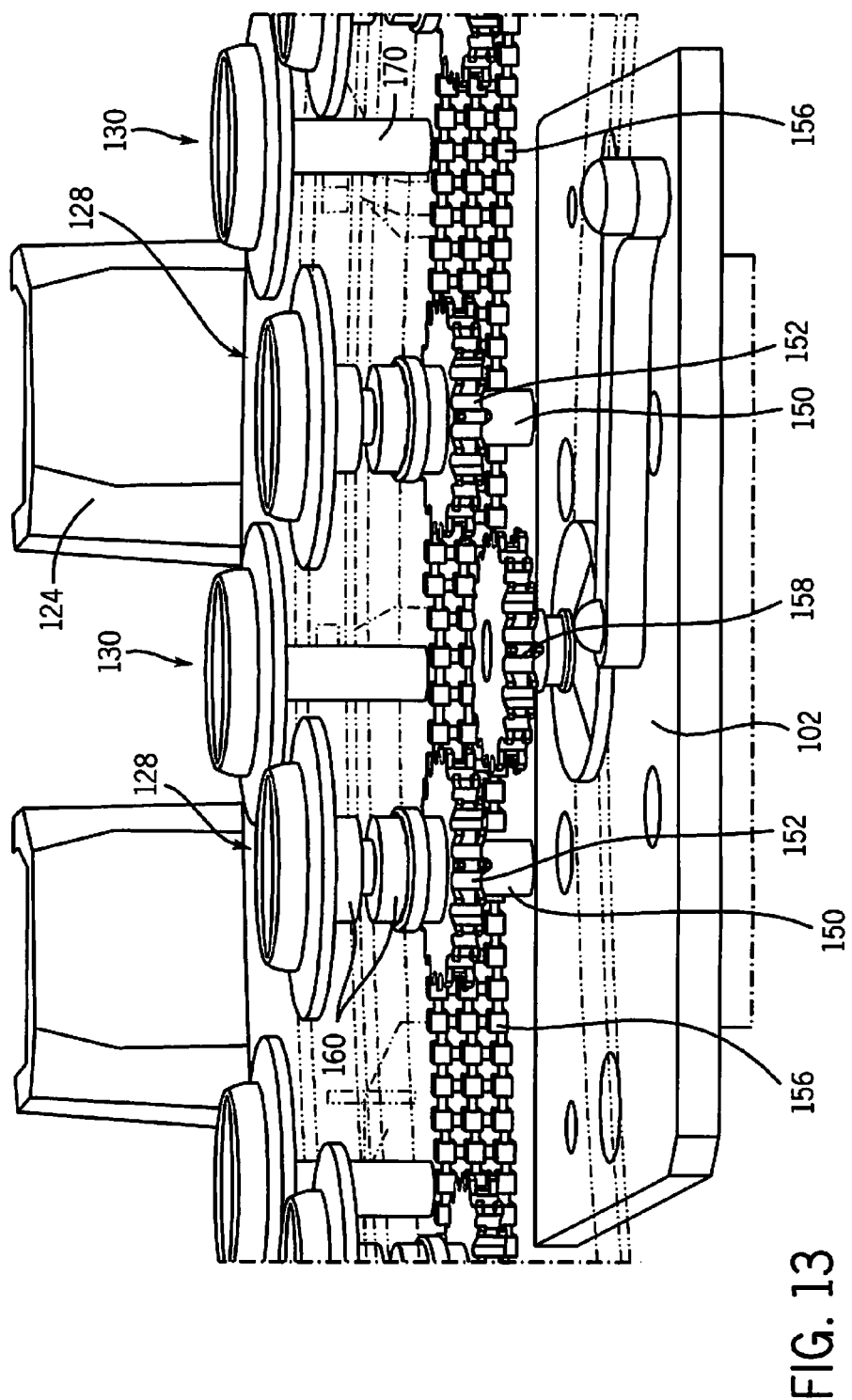
FIG. 13 is a perspective view illustrating the chain, the drive sprocket wheel, the sprocket wheels attached to the shafts of rotatable seats, bearings attached to the shafts of rotatable seats, rotatable seats, and fixed seats.

The carousel 102 further contains a plurality of resiliently biased retention elements 132. See also FIG. 10. These retention elements 132 help retain oversized test kit containers when they are used. One material suitable for forming the retention element 132 is a polyimide thermoplastic resin, which is commercially available under the trademark "Ultem 2300."

In addition, the carousel 102 has a target 140 for positional calibration of the filling systems with respect to the carousel 102 (see FIG. 3). A further addition to the carousel 102 is the pin 142 at the home location (see FIG. 4). This pin 142 trips a home sensor (not shown) in order to enable location of the home position of the carousel 102.

Figure 5:
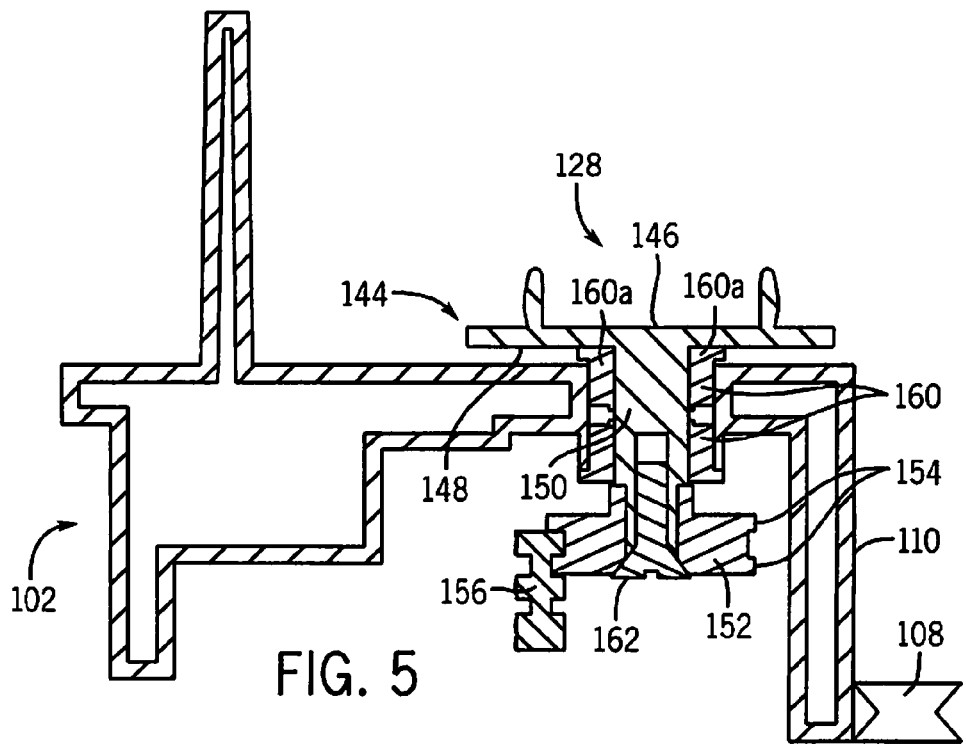
FIG. 5 is a schematic view, in cross-section, showing the carousel, the rotatable seat, the chain, the sprocket wheel attached to the shaft of a rotatable seat, and bearings attached to the shaft of a rotatable seat.
Figure 6:
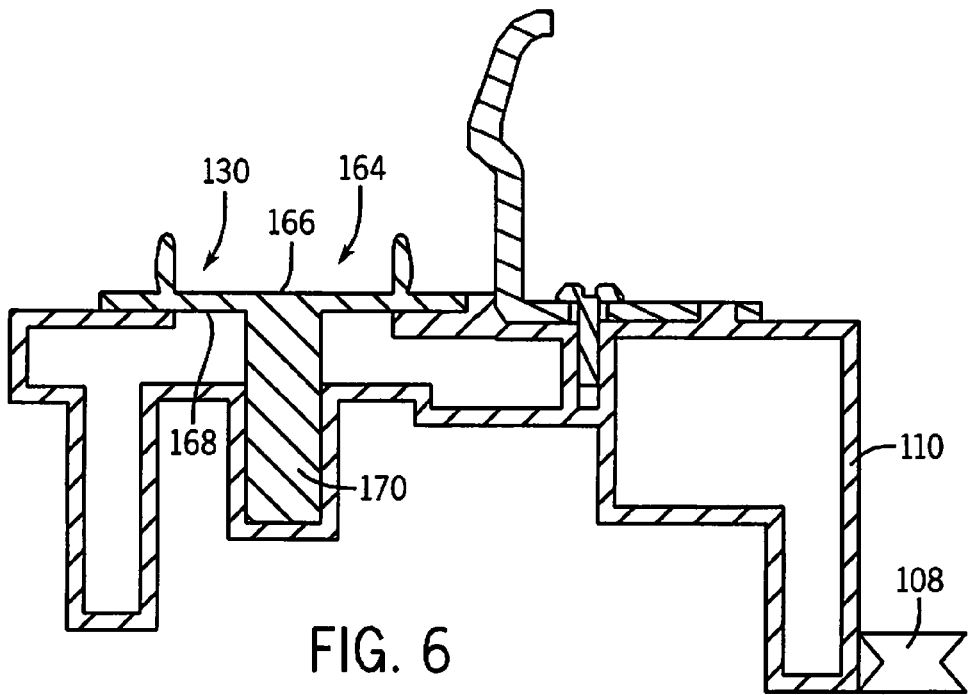
FIG. 6 is a schematic view, in cross-section, showing the carousel, a fixed seat, and a retention element for securing oversized containers.
Figure 7A:
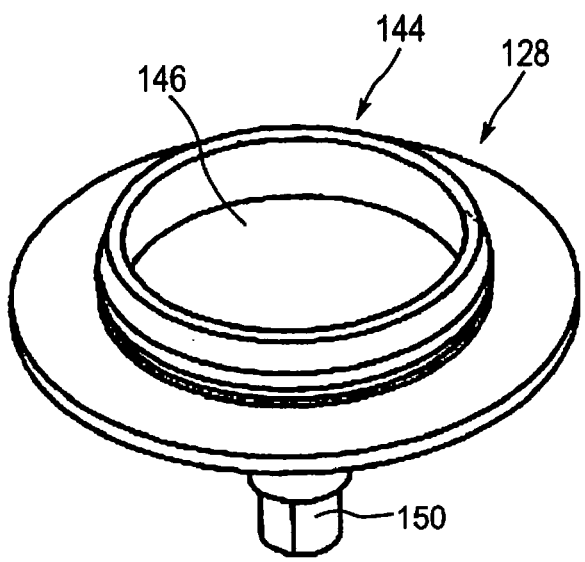
FIG. 7A is a perspective view of a seat suitable for a rotatable seat.
Figure 8:
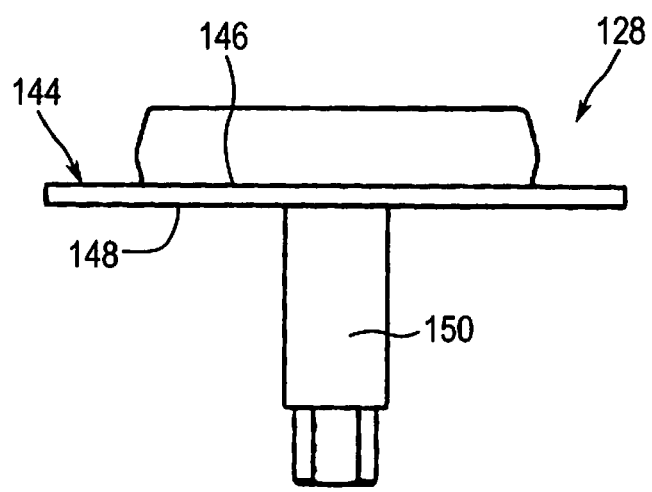
FIG. 8 is a side view in elevation of the rotatable seat of FIG. 7A.

Referring to FIGS. 2, 3, 4, 5, 6, 7A, 7B, 8, 9, 11, 12, and 13, the carousel 102 contains a plurality of rotatable seats 128 for reagent containers. Each rotatable seat 128 comprises a platform 144 having a top surface 146 and a bottom surface 148. A reagent container can be mounted on the top surface 146 of the platform 144 of the seat 128. In general, the mounting procedure is shown in FIGS. 24A and 24B of U.S. Pat. No. 6,562,298, previously incorporated herein by reference. Each rotatable seat 128 has a shaft 150 projecting from bottom surface 148 thereof. Upon the shaft 150 is mounted at least one sprocket wheel 152, which contains a plurality of sprockets 154. Attached to the end of the shaft 150 by a fastener 162, e.g., a screw, is a sprocket wheel 152. In one embodiment, the sprockets 154 can be placed in a single row. In alternative embodiments, two or more rows of sprockets 154 can be placed on the sprocket wheel 152. The sprockets 154 are designed to engage the links of a chain 156. When the drive sprocket wheel 158 is actuated by a motor so as to be caused to rotate about its own axis, the drive sprocket wheel 158 causes the chain 156 to move, whereby the chain 156, in turn, causes the sprocket wheels 152 to rotate about their respective axes. Rotation of the sprocket wheels 152 causes rotation of the shafts 150, which cause the rotatable seats 128 to rotate about their respective axes. In this manner, the contents of the containers containing the solid-phase reagent can be agitated to bring about homogeneity of the solid-phase reagent. The drive sprocket wheel 158 is similar to the sprocket wheels 152 in that the drive sprocket wheel 158 contains a plurality of sprockets 154', but the drive sprocket wheel 158 is not associated with a rotatable seat 128 for supporting a reagent container. At least one bearing 160, which is located on the shaft 150 of the sprocket wheel 152, is employed to allow the rotatable seat 128 to be easily rotated. As shown in FIG. 5, the rotatable seat 128 is supported by two ball bearings 160. In the embodiment shown in FIG. 5, it can be seen that the bearing 160 is supported on the carousel 102 by a flange 160a. A single rotatable seat 128 can be a unitary piece and be made from a bar of stainless steel as shown in FIGS. 7A and 8. Rotatable seats 128 can also be formed from an assembly of individual components, e.g., platform, shaft, ring-shaped projection. Each of the seats 128 is adapted to receive a reagent container that contains a reagent that requires agitation.

Figure 7B:
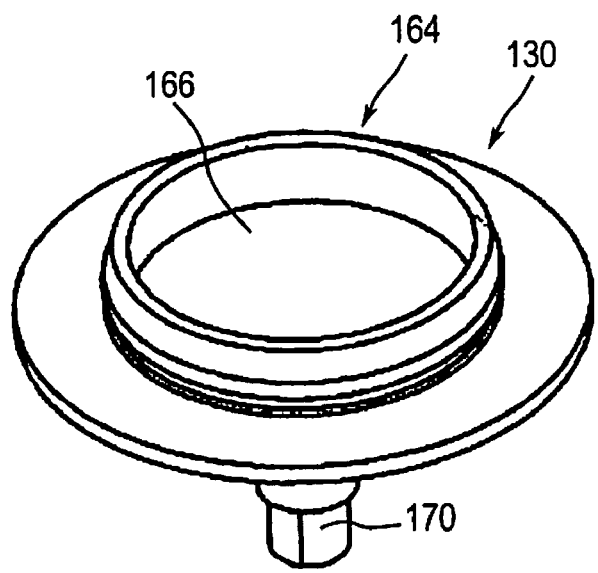
FIG. 7B is a perspective view of a seat suitable for a fixed seat.
Figure 9:
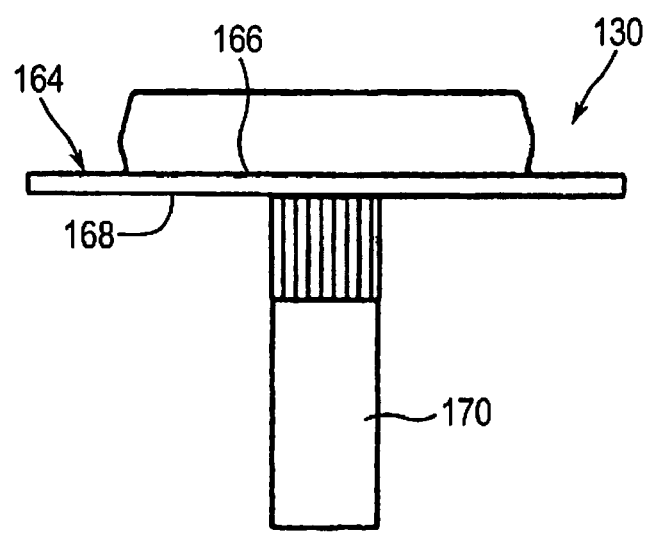
FIG. 9 is a side view in elevation of the fixed seat of FIG. 7B.

The carousel 102 is shown to contain a plurality of fixed seats 130 arranged in a circle concentric with the rotatable seats 128. These fixed seats 130 can be used to support reagents that do not need to be agitated (tracer or labeled) or assay specific diluents that do not need to be agitated. Each fixed seat 130 comprises a platform 164 having a top surface 166 and a bottom surface 168. A reagent container can be mounted on the top surface 166 of the platform 164 of the fixed seat 130. In general, the mounting procedure is shown in FIGS. 24A and 24B of U.S. Pat. No. 6,562,298, previously incorporated herein by reference. Each fixed seat 130 has a shaft 170 projecting from bottom surface 168 thereof. The fixed seat 130 is press fitted to the carousel 102 by means of the shaft 170. A single fixed seat 130 can be a unitary piece made from a bar of stainless steel as shown in FIGS. 7B and 9. Fixed seats 130 can also be formed from an assembly of individual components, e.g., platform, shaft, ring-shaped projection. Each of the seats 130 is adapted to receive a reagent container that does not require agitation.

Figure 14:
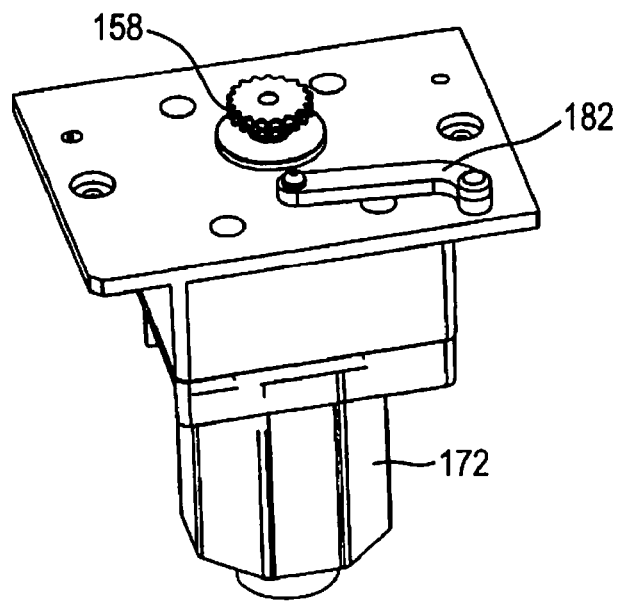
FIG. 14 is a perspective view of a cam assembly for engaging the drive sprocket wheel and the chain and disengaging the drive sprocket wheel from the chain.
Figure 15:
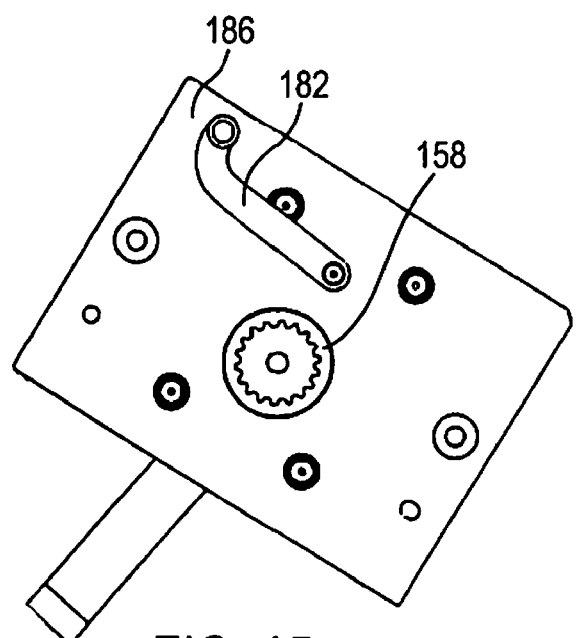
FIG. 15 is a top plan view of the cam assembly of FIG. 14.
Figure 16:
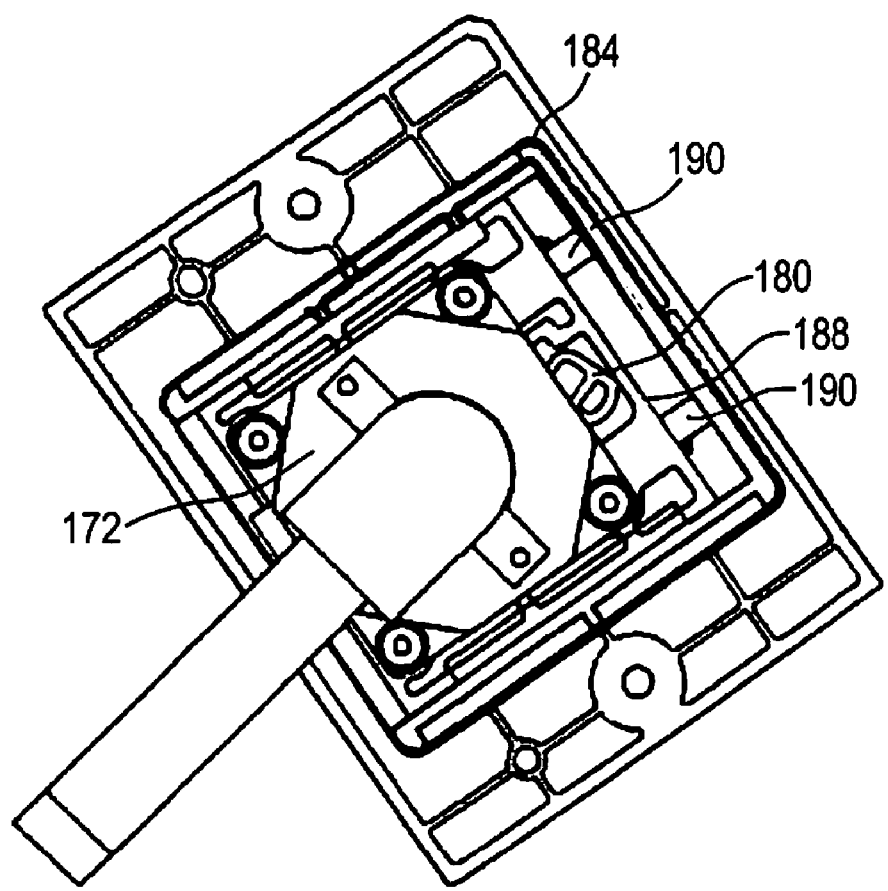
FIG. 16 is a bottom plan view of the cam assembly of FIG. 14.

In the embodiment shown in FIGS. 2 through 6, inclusive, and 13, a motor 172, separate from the motor 106 for driving the carousel 102 about the central axis of the carousel 102, is employed to cause the drive sprocket wheel 158 to rotate about the axis of the drive sprocket wheel 158. This motor 172 is shown in FIGS. 1B, 14, and 16. In FIG. 1B, the motor 172 is designated by the reference character "M". In the present invention, the motor 172 drives a drive sprocket wheel 158 and does not drive a satellite gear "$S_0$" that rotates a ring gear "R" that causes other satellite gears "$S_1, S_2, \ldots, S_n$" to rotate.

The particular dimensions of the foregoing components are not critical. However, certain dimensions will be disclosed to indicate the order of magnitude of the components of one embodiment of this invention.

A suitable nominal diameter of the carousel 102 can range from about 18 to 24 inches. The nominal height of the carousel 102 can range from about two to four inches.

Nominal dimensions of a typical seat for a reagent container can range from 0.9 to 1.0 inches in diameter for the ring-shaped projection that mates with gripping fingers at the base of the reagent container; one to two inches in diameter for the platforms 144 and 164; 0.7 to 0.9 inch for the length of the drive shaft 150 and 0.9 to 1.1 inches for the length of the drive shaft 170. However, the foregoing dimensions are merely examples, and one of ordinary skill in the art can select alternative dimensions for carrying out the intended purpose of the invention.

The drive sprocket wheel 158 is mounted over the motor 172. The number of sprockets 154' on the drive sprocket wheel 158 is not critical. The actual number of sprockets is specific to a particular design and depends upon link spacing in the chain, diametric pitch, space available for locating the sprocket wheel, availability of commercially available and customized components, diameter upon which the centerlines of the rotatable seats 128 are located, stretchability of the chain, operating temperature, coefficient of thermal expansion of the materials used, and the like. One having ordinary skill in the art can readily specify these features without undue experimentation. Similarly, the number of sprockets 154 on the sprocket wheels 152 is not critical and is dependent upon the same factors described previously for determining the actual number of sprockets 154' on the drive sprocket wheel 158.

At least one row of sprockets 154' on the drive sprocket wheel 158 is required. More than one row of sprockets 154' can be used. Additional rows of sprockets 154' can be added. The use of additional rows is dependent upon space constraints and design needs. As more rows are utilized, chain wear is reduced. Similarly, at least one row of sprockets 154 on the sprocket wheel 152 is required. More than one row of sprockets 154 can be used. Additional rows of sprockets 154 can be added. The use of additional rows is dependent upon space constraints and design needs. As more rows are utilized, chain wear is reduced The primary difference between the drive sprocket wheel 158 and the sprocket wheels 152 is the manner in which they are attached to components to which they are adjacent. In the embodiment described herein, the drive sprocket wheel 158 is attached to the shaft of the motor 172 by a press fit. A sprocket wheel 152 associated with a rotatable seat 128 is attached to the shaft 150, which is typically an elongated element having a D-shaped cross-section, by means of a fastener 162, e.g., a screw (see FIG. 5). The drive sprocket wheel 158 is set at a different height from the sprocket wheels 152 attached to the shafts 150 projecting from the bottom surfaces 148 of the platforms 144, in order to prevent interference. The diametric pitches of the drive sprocket wheel 158 and the sprocket wheels 152 are typically the same; however the diametric pitches of the drive sprocket wheel 158 and the sprocket wheels 152 can vary by multiples of 2.

The number of strands in the chain 156 is not critical. The number of strands in the chain 156 can be specified by the designer, and the material of the chain 156 can be specified by the designer. Of course, the designer is one of ordinary skill in the art. The chain 156 shown in FIGS. 6 and 13 has three strands. Some materials require no reinforcing strands. Other materials call for reinforcing strands.

The length of the chain 156 is not critical. The actual length is dependent upon design parameters and is specified on the basis of diametric pitch, pitch diameter of the sprockets, diameter upon which the centerlines of the sprocket wheels are located, chain stretchability, operating temperature, coefficient of thermal expansion of the materials used, etc. Ultimate tensile strength, temperature range, operating load, operating speed, and weight can be specified by one of ordinary skill in the art. Dual ladder chains can be used.

The number of drive pins on the chain 156 is not critical. The actual number of drive pins is specific to a particular design and depends upon link spacing in the chain, diametric pitch, space available for locating the sprocket wheel, availability of commercially available and customized components, diameter upon which the centerlines of the sprocket wheels 152 are located, stretchability of the chain, operating temperature, coefficient of thermal expansion of the materials used, and the like. One having ordinary skill in the art can readily specify these features without undue experimentation.

Chains 156 suitable for use for this invention are commercially available under the trademark PIC® Design and are commercially available from W. M. Berg, Inc., East Rockaway, N.Y. One type of chain has a stainless steel core having a coating of molded polyurethane. The number of drive pins can vary. The length of the chain can vary. See, for example, No-Slip Positive Drive Belt data sheet, from PIC® Design, incorporated herein by reference, and MIN-E-PITCH® Dual Ladder Chain data sheets from W. M. Berg, Inc. The foregoing data sheet discloses chains having from 30 to 440 drive pins, spliced lengths of from 4.712 inches to 69.115 inches, bulk lengths of from 5 to 100 feet. These chains can have either an Aramid fiber Kevlar core(s) (FLA-Series) or a stainless steel core(s) (FLS-Series) and a molded polyurethane coating. The Aramid fiber core provides highest flexibility and speed; the stainless steel core provides lowest stretch. Typical dimensions for a chain designated as a triple core belt (F20TS-Series, F20TS-XX-Series (PIC® Design)) are 0.15708 inch circular pitch, three strands, width of 0.375 inch, 0.070 pin diameter, 1/16 inch between strands. Design specifications from W. M. Berg, East Rockaway, N.Y. are substantially similar to those from PIC® Design. For the carousel 102 described herein, the chain 156 typically has chains having from 360 to 370 drive pins and a spliced length of from 56.548 inches to 58.119 inches. However, these parameters can vary, based on the circumference of the carousel 102, the number of sprocket wheels 152, and other design factors.

The chain 156 can provide smooth and quiet operation. The chain need not be lubricated. A linked chain, such as, for example, a bicycle chain, could conceivably be used in place of the coated chains commercially available from PIC® Design and from W. M. Berg, East Rockaway, N.Y.

Selection of motors is determined by the designer and is dependent on choices made about the manner desired for the chain 156 and the carousel 102 to be driven. Suitable motors can readily be selected by one of ordinary skill in the art. The drive sprocket wheel 158 can be driven by means of a motor 172, e.g., a stepper motor. A typical motor suitable for use in this invention has a coil resistance of 0.38±10% ohms, 1.8 degree±3% step angle, operates off 36 volt power, is pulse width modulated, rated at 2.5 amps per coil, and has an encoder mounted to it. Such a motor is manufactured by Pacific Scientific and has the designation P/N P22NSXA-LSS-SS-07. The encoder can be a HP encoder P/N HEDL-5600-H06.

The stepper motor 172 is reversible and controlled by a central processing unit (not shown). The stepper motor 172 functions to cause the drive sprocket wheel 158, the chain 156, and the sprocket wheels 152 to rotate the drive shafts 150 of the rotatable seats 128 at specified intervals of time. The rotation imparted to the drive shafts 150 of the rotatable seats 128 provide the necessary motion to rotate the reagent containers for enabling the fins to agitate the dispersions of solid-phase reagents within the reagent containers and thereby maintain uniform concentrations of the solid-phase reagents within the dispersions in the reagent containers.

Actuation of the motor 172 causes the drive sprocket wheel 158 to drive the chain 156, which causes the sprocket wheels 152 to rotate, which ultimately causes the rotatable seats 128 to rotate about their respective axes.

The motor 106 for the driving the carousel 102 is fixed to a motor mount (not shown) on the base. The motor 172 for driving the chain 156 is fixed to a motor mount (not shown) on the base.

Both motors 106 and 172 are located beneath the carousel 102, as they are in ARCHITECT i2000/i2000SR apparatus. See FIG. 1B. The centerline of the motor 172 for driving the drive sprocket wheel 158 is located in such a way as to cause the drive sprocket wheel 158 to engage the chain 156 when a handle enables a cam to be positioned so that the chain 156 is engaged with the drive sprocket wheel 158.

A cam 180 can be employed to engage and disengage the chain 156 from the drive sprocket wheel 158. The cam 180 is operated by a handle 182 and is supported by an interface plate 184 and a mounting plate 186. When the cam 180 rotates, it presses against a motor mounting plate 188. The motor mounting plate 188 is spring loaded against the interface plate 184. As the cam 180 rotates, the motor mounting plate 188 slides laterally, and the springs 190 are further compressed. The motor 172 is attached the motor mounting plate 188, and the drive sprocket wheel 158 is attached to the motor 172. The action of the cam 180 disengages the drive sprocket wheel 158 from the chain 156. Moving the handle 182 back allows the springs 190 to push the motor mounting plate 186 to a position whereby the springs 190 are uncompressed, thereby re-engaging the drive sprocket wheel 158 with the chain 156. One fastener, e.g., a screw, attaches the handle 182 to the cam 180. Four fasteners, e.g., screws, attach the motor 172 to the motor mounting plate 186. Four additional fasteners, e.g., screws, attach the interface plate 184 to the motor mounting plate 186. The handle 182 is operated by hand.

Operation

The operator loads required assay reagents, in machine-readable labeled containers, into the appropriate seats (rotatable for solid-phase reagents or fixed for labeled or tracer reagents) on the carousel in any order. The analyzer will read all labels before initiating a run, identifying each reagent, its position, its lot number, and expiration date. U.S. Pat. No. 6,562,298 describes how an assay can be performed. With respect to the reagent transport apparatus, when it is desired to agitate the contents of the reagent containers seated in the rotatable seats 128, the drive sprocket wheel 158 is engaged with the chain 156. The motor 172 is then actuated to impart oscillating motion to the chain 156, which in turn imparts oscillating motion to the sprocket wheels 152, which cause the rotatable seats 128 to rotate, thereby agitating the contents of the reagent containers seated on the rotatable seats 126. The motor 172 is reversible, so that the rotatable seats can be rotated both clockwise and counter-clockwise, thereby rotating the contents of the reagent containers seated on the rotatable seats clockwise and counter-clockwise.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A reagent transport apparatus for use on a clinical analyzer, said apparatus comprising:
    (a) a base;
    (b) a carousel mounted on the base for rotation about a first vertical axis;
    (c) a drive motor for rotating the carousel about the first vertical axis;
    (d) a control unit for operating the drive motor to selectively position a selected reagent container at a reagent aspiration position;
    (e) a plurality of seats for supporting containers for holding contents for agitation, the plurality of seats arranged in a first circle on the carousel, the seats concentric with the first vertical axis, each of the seats having a second vertical axis;
    (f) an agitating motor for rotating each of the plurality of seats for supporting containers for holding contents for agitation;
    (g) a drive sprocket wheel having a plurality of sprockets, the drive sprocket wheel coupled to the agitating motor, the drive sprocket wheel engaging and driving a chain;
    (h) a plurality of sprocket wheels, each of said plurality of sprocket wheels having a plurality of sprockets, each of said plurality of sprocket wheels having a second vertical axis, each of said plurality of sprocket wheels being rotated by the chain about its second vertical axis; whereby rotation of the drive sprocket wheel causes driving of the chain, which in turn causes rotation of the sprocket wheels, each of the sprocket wheels wheel being rotated about its respective second vertical axis, thereby rotating the seats for supporting containers for holding contents for agitation, each seat being rotated about its respective second vertical axis, the reagent transport apparatus further including a cam for engaging and disengaging the chain and the drive sprocket wheel and a handle for moving the cam.

2. The reagent transport apparatus of claim 1, wherein the carousel further includes a plurality of seats for holding containers that contain materials that do not require agitation.

3. The reagent transport apparatus of claim 1, wherein each of the containers has at least one agitator fin molded into the inner wall thereof.

4. The reagent transport apparatus of claim 1, wherein the agitating motor is reversible.

5. The reagent transport apparatus of claim 1, wherein the content of the container to be agitated is a solid-phase reagent.

6. The reagent transport apparatus of claim 1, further comprising a second carousel mounted on the base for rotation about the first vertical axis.

\* \* \* \* \*